(12) United States Patent
Lee et al.

(10) Patent No.: US 7,582,718 B2
(45) Date of Patent: Sep. 1, 2009

(54) MULTI-FUNCTIONAL LINEAR SILOXANE COMPOUND, A SILOXANE POLYMER PREPARED FROM THE COMPOUND, AND A PROCESS FOR FORMING A DIELECTRIC FILM BY USING THE POLYMER

(75) Inventors: Jae Jun Lee, Gyeonggi-Do (KR); Jong Baek Seon, Gyeonggi-Do (KR); Hyun Dam Jeong, Gyeonggi-Do (KR); Jin Heong Yim, Daejeon-Si (KR); Hyeon Jin Shin, Gyeonggi-Do (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 293 days.

(21) Appl. No.: 10/868,222

(22) Filed: Jun. 16, 2004

(65) Prior Publication Data

US 2005/0131190 A1    Jun. 16, 2005

(30) Foreign Application Priority Data

Dec. 13, 2003    (KR) ...................... 10-2003-0090909

(51) Int. Cl.
*C08G 77/60* (2006.01)
(52) U.S. Cl. .............................. 528/35; 528/31; 528/32
(58) Field of Classification Search .................. 528/35, 528/31, 32
See application file for complete search history.

(56) References Cited

U.S. PATENT DOCUMENTS

| | | | |
|---|---|---|---|
| 3,615,272 A | 10/1971 | Collins et al. | |
| 4,399,266 A | 8/1983 | Matsumura et al. | |
| 4,756,977 A | 7/1988 | Haluska et al. | |
| 4,999,397 A | 3/1991 | Weiss et al. | |
| 5,010,159 A | 4/1991 | Bank et al. | |
| 5,378,790 A | 1/1995 | Michalczyk et al. | |
| 5,853,808 A | 12/1998 | Arkles et al. | |
| 6,000,339 A | 12/1999 | Matsuzawa | |
| 6,232,424 B1 | 5/2001 | Zhong et al. | |

FOREIGN PATENT DOCUMENTS

| | | |
|---|---|---|
| EP | 0997497 A1 | 5/2000 |
| KR | 10-0343938 B1 | 6/2002 |

*Primary Examiner*—Kuo-Liang Peng
(74) *Attorney, Agent, or Firm*—Harness, Dickey & Pierce, P.L.C.

(57) ABSTRACT

A novel multi-functional linear siloxane compound, a siloxane polymer prepared from the siloxane compound, and a process for forming a dielectric film by using the siloxane polymer. The linear siloxane polymer has enhanced mechanical properties (e.g., modulus), superior thermal stability, a low carbon content and a low hygroscopicity and is prepared by the homopolymerization of the linear siloxane compound or the copolymerization of the linear siloxane compound with another monomer. A dielectric film can be produced by heat-curing a coating solution containing the siloxane polymer which is highly reactive. The siloxane polymer prepared from the siloxane compound not only has satisfactory mechanical properties, thermal stability and crack resistance, but also exhibits a low hygroscopicity and excellent compatibility with pore-forming materials, which leads to a low dielectric constant. Furthermore, the siloxane polymer retains a relatively low carbon content but a high $SiO_2$ content, resulting in its improved applicability to semiconductor devices. Therefore, the siloxane polymer is advantageously used as a material for dielectric films of semiconductor devices.

1 Claim, No Drawings

MULTI-FUNCTIONAL LINEAR SILOXANE COMPOUND, A SILOXANE POLYMER PREPARED FROM THE COMPOUND, AND A PROCESS FOR FORMING A DIELECTRIC FILM BY USING THE POLYMER

BACKGROUND OF THE INVENTION

This non-provisional application claims priority under 35 U.S.C. § 119(a) on Korean Patent Application No. 2003-90909 filed on Dec. 13, 2003, which is herein incorporated by reference.

1. Field of the Invention

The present invention relates to a novel multi-functional linear siloxane compound, a siloxane polymer prepared from the siloxane compound, and a process for forming a dielectric film by using the siloxane polymer. More particularly, the present invention relates to a novel multi-functional linear siloxane compound which can be changed into a polymer having advantageous mechanical properties, e.g., modulus, superior thermal stability, a low carbon content and a low hygroscopicity; a siloxane polymer prepared by the homopolymerization of the linear siloxane compound or the copolymerization of the linear siloxane compound with another monomer; and a process for forming a dielectric film which comprises the step of heat-curing a coating solution containing the siloxane polymer.

2. Description of the Related Art

In recent years, as the integration density of semiconductor integrated circuits has increased, the transmission of electric signals between wirings has slowed due to an increased RC delay. For this reason, there is a growing interest in lowering the capacitance of interlayer insulating thin films for semiconductor devices. For example, U.S. Pat. Nos. 3,615,272, 4,399,266, 4,756,977 and 4,999,397 disclose polysilsesquioxane dielectric films having a dielectric constant of about 2.5~3.1 which can be formed by spin-on-deposition (SOD). The polysilsesquioxane dielectric films can replace conventional $SiO_2$ dielectric films which have a dielectric constant of about 4.0), formed by chemical vapor deposition (CVD). On the other hand, hydrogen silsesquioxanes and a number of preparation processes thereof are well known in the art. For example, U.S. Pat. No. 3,615,272 teaches a process for preparing a completely condensed hydrogen silsesquioxane by condensing trichloro-, trimethoxy- or triacetoxysilane in a sulfuric acid medium. Further, U.S. Pat. No. 5,010,159 discloses a process for preparing a hydrogen silsesquioxane by hydrolyzing a hydridosilane in an arylsulfonic acid hydrate-containing hydrolysis medium to form a resin, and contacting the resin with a neutralizing agent. Further, U.S. Pat. No. 6,232,424 suggests a highly soluble silicone resin composition having excellent solution stability which is prepared by hydrolyzing and condensing a tetraalkoxysilane, an organosilane and an organotrialkoxysilane in the presence of water and a catalyst. U.S. Pat. No. 6,000,339 reports a process for preparing a silica-based compound which has improved oxygen plasma resistance and other physical properties, and enables the formation of a thick-layer. According to this process, the silica-based compound is prepared by reacting a monomer selected from alkoxysilanes, fluorine-containing alkoxysilanes and alkylalkoxysilanes with an alkoxide of titanium (Ti) or zirconium (Zr) in the presence of water and a catalyst. U.S. Pat. No. 5,853,808 discloses siloxane and silsesquioxane polymers useful for preparing $SiO_2$-rich thin films wherein the polymers are prepared from organosilanes having a β-substituted reactive group, and the thin film compositions containing these polymers. Also, alkoxysilane compositions and insulating thin films formed by using these compositions are described in EP 0 997 497 A1. These compositions are obtained by hydrolyzing and condensing a mixture of at least one alkoxysilane selected from monoalkoxysilanes, dialkoxysilanes, trialkoxysilanes, tetraalkoxysilanes and trialkoxysilane dimers. In addition, U.S. Pat. No. 5,378,790 discloses organic/inorganic hybrid materials having excellent physical properties. Korean Patent No. 343938 discloses a siloxane composition prepared by hydrolyzing and condensing a cyclic siloxane monomer, and a dielectric thin film formed by using this composition.

However, dielectric thin films formed by using the siloxane polymers prepared from the prior art have the problem of an insufficiently low dielectric constant. Because they have a low dielectric constant, they possess poor mechanical properties. Additionally, they exhibit a limited applicability to semiconductor processes due to a high organic carbon content. In particular, in the case of a polymer prepared from a "Q"-shaped Si compound such as tetramethoxysilane, there is the problem of a high hygroscopicity, despite a low organic carbon content and good mechanical properties in the dielectric films, causing a drastic increase in the dielectric constant. Accordingly, the polymer has limited applicability to dielectric films, particularly those formed by the SOD process. In recent years, there has been an increased demand for combining siloxane polymers highly compatible with pore-forming materials so as to create a lower dielectric constant.

Thus, there is a need in the art to develop a material for forming a dielectric film by the SOD process which has a low dielectric constant, superior mechanical properties, e.g., modulus, excellent compatibility with pore-forming material, and markedly improved applicability to semiconductor processes, due to a low carbon content.

SUMMARY OF THE INVENTION

Research has been intensively conducted to solve the above-mentioned problems. As a result, the present inventors have found that a multi-functional linear siloxane compound with a particular structure is excellent in reactivity, and if necessary, can be easily formed into a ladder structure when polymerized. The present inventors have also found that a siloxane polymer prepared by the homopolymerization of the multi-functional linear siloxane compound, or the copolymerization of the siloxane compound with another siloxane- or silane-based monomer, exhibits excellent mechanical properties, thermal stability and crack resistance, is highly compatible with conventional pore-forming materials, and maintains its hygroscopicity at a low level even during the SOD process, thus ensuring excellent insulating characteristics, and retaining a relatively low carbon content but a high $SiO_2$ content, resulting in an improved applicability to semiconductor processes. The present invention is based on these findings.

Therefore, it is a feature of the present invention to provide a multi-functional siloxane compound which can impart excellent mechanical properties, thermal stability, insulating properties and crack resistance to a dielectric film.

It is another feature of the present invention to provide a siloxane polymer or copolymer prepared from the multi-functional siloxane compound.

It is yet another feature of the present invention to provide a process for forming a dielectric film by using the siloxane polymer or copolymer.

In accordance with the features of the present invention, there is provided a multi-functional linear siloxane compound represented by Formula 1 below:

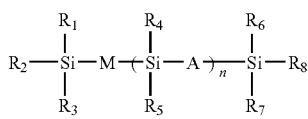

Formula 1 wherein $R_1$, $R_2$, $R_3$, $R_4$, $R_5$, $R_6$, $R_7$ and $R_8$ are each independently a hydrogen atom, a $C_{1-3}$ alkyl group, a $C_{3-10}$ cycloalkyl group, a $C_{2-3}$ alkenyl group, a $C_{6-15}$ aryl group, a $C_{1-10}$ alkoxy group, a $C_{1-10}$ acyloxy group, a $C_{1-10}$ silyloxy group or a halogen atom, at least one of these substituents is a hydrolysable functional group; M is an oxygen atom or a $C_{1-3}$ alkylene group; n is an integer between 1 and 20; and A is an oxygen atom or a $C_{1-3}$ alkylene group, at least one A is different from M, provided that when n is 2 or more, each A is the same or different.

In accordance with the features of the present invention, there is further provided a siloxane polymer which is prepared by the hydrolysis and polycondensation of the multi-functional linear siloxane compound in an organic solvent in the presence of water and an acid or base catalyst.

In accordance with the features of the present invention, there is further provided a siloxane copolymer which is prepared by the hydrolysis and polycondensation of the multi-functional linear siloxane compound with another siloxane- or silane-based monomer, in an organic solvent in the presence of water and an acid or base catalyst.

In accordance with the features of the present invention, there is yet further provided a process for forming a dielectric film by using the siloxane polymer or copolymer.

DESCRIPTION OF THE PREFERRED EMBODIMENTS

Hereinafter, the present invention will be explained in more detail.

Multi-Functional Linear Siloxane Compound

The linear siloxane compound of Formula 1 according to the present invention may have a plurality of reactive groups according to the intended purpose, and thus facilitates the formation into a ladder structure depending on its structure when polymerized. Accordingly, the polymer can exhibit excellent mechanical properties (e.g., high toughness and modulus) because of its ladder structure. Appropriate choice of M and A in Formula 1 causes a substantial reduction in carbon content, a decrease in CTE (coefficient of thermal expansion) and considerable reduction in the content of alkoxy groups in the polymers to be prepared, thereby enabling the preparation of polymers almost devoid of moisture absorption.

Preferred linear siloxane compounds of the present invention are those represented by Formulae 2 to 4 below:

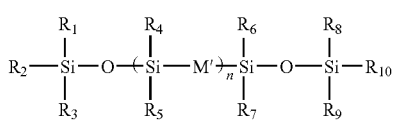

Formula 2 wherein M' is a $C_{1-3}$ alkylene group; $R_1$, $R_2$, $R_3$, $R_4$, $R_5$, $R_6$, $R_7$, $R_8$, $R_9$ and $R_{10}$ are each independently a hydrogen atom, a $C_{1-3}$ alkyl group, a $C_{3-10}$ cycloalkyl group, a $C_{2-3}$ alkenyl group, a $C_{6-15}$ aryl group, a $C_{1-10}$ alkoxy group, a $C_{1-10}$ acyloxy group, a $C_{1-10}$ silyloxy group or a halogen atom, at least three of these substituents are hydrolysable functional groups; and n is an integer between 1 and 20;

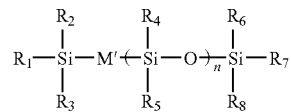

Formula 3 wherein M', $R_1$, $R_2$, $R_3$, $R_4$, $R_5$, $R_6$, $R_7$, $R_8$ and n are as defined in Formula 2; and

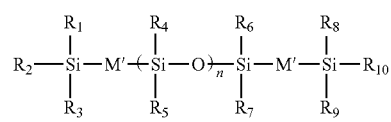

Formula 4 wherein M', $R_1$, $R_2$, $R_3$, $R_4$, $R_5$, $R_6$, $R_7$, $R_8$, $R_9$, $R_{10}$ and n are as defined in Formula 2.

More preferably, the multi-functional linear siloxane compound of the present invention is represented by any one of Formulae 5 to 7 below:

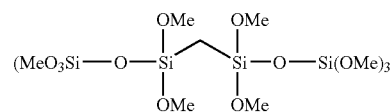

Formula 5

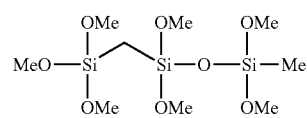

Formula 6

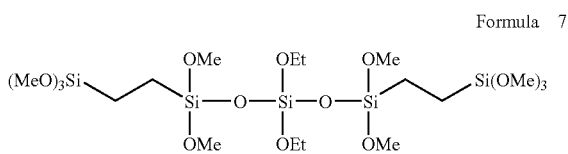

Formula 7

Polymers prepared from "Q"-shaped Si compounds generally exhibit excellent mechanical properties, but involve an increase in dielectric constant due to their high hygroscopicity. In contrast, although the linear siloxane compound of the present invention, (e.g., the compound of Formula 7) may have a "Q"-shaped structure incorporated in the backbone chain, it can maintain the hygroscopicity at a very low level, which leads to superior insulating characteristics, and has good compatibility with conventional pore-forming materials and excellent mechanical properties.

The linear siloxane compound of the present invention can be prepared through suitable synthetic pathways depending on its structure. For instance, the compounds of Formulae 5 to 7 can be prepared in accordance with Reaction Schemes 1 to 3 below:

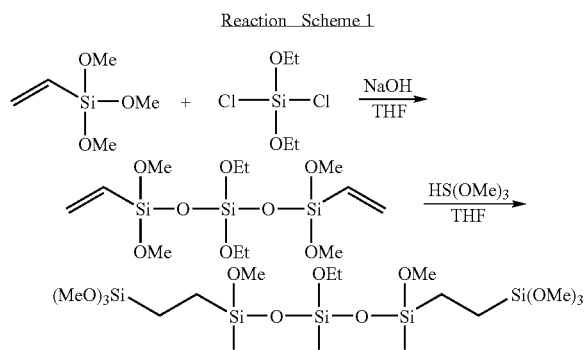

Reaction Scheme 1

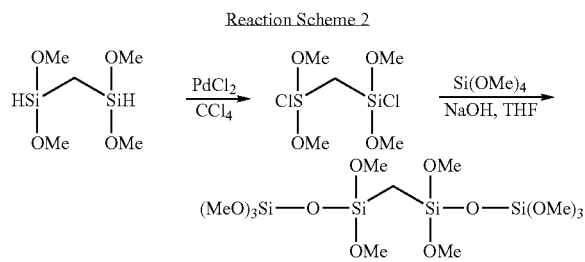

Reaction Scheme 2

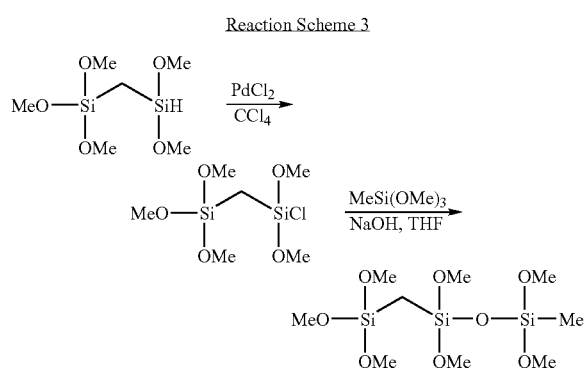

Reaction Scheme 3

Siloxane Polymer

Additionally, the present invention provides a siloxane polymer prepared by the polymerization of the multi-functional linear siloxane compound, optionally with at least one monomer selected from compounds represented by Formulae 8 to 11 below:

Formula 8

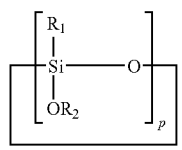

wherein $R_1$ is a hydrogen atom, a $C_{1-3}$ alkyl group, a $C_{1-3}$ alkoxy group or a $C_{6-15}$ aryl group; $R_2$ is a hydrogen atom, a $C_{1-10}$ alkyl group or $SiX_1X_2X_3$ (in which $X_1$, $X_2$ and $X_3$ are each independently a hydrogen atom, a $C_{1-3}$ alkyl group, a $C_{1-10}$ alkoxy group or a halogen atom, at least one of these substituents is a hydrolysable functional group); and p is an integer between 3 and 8;

Formula 9

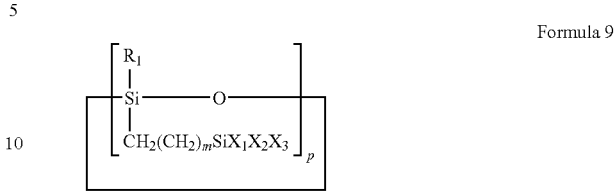

wherein $R_1$ is a hydrogen atom, a $C_{1-3}$ alkyl group or a $C_{6-15}$ aryl group; $X_1$, $X_2$ and $X_3$ are each independently a hydrogen atom, a $C_{1-3}$ alkyl group, a $C_{1-10}$ alkoxy group or a halogen atom, at least one of these substituents is a hydrolysable functional group; m is an integer between 0 and 10; and p is an integer between 3 and 8; and Formula 10

$$X_3X_2X_1Si\text{-}M\text{-}SiX_1X_2X_3$$

wherein $X_1$, $X_2$ and $X_3$ are each independently a hydrogen atom, a $C_{1-3}$ alkyl group, a $C_{1-10}$ alkoxy group or a halogen atom, at least one of these substituents is a hydrolysable functional group; M is a $C_{1-10}$ alkylene or $C_{6-15}$ arylene group; and Formula 11

$$(A')_nSi(B')_{4-n}$$

wherein A' is a hydrogen atom, a $C_{1-3}$ alkyl group or a $C_{6-15}$ aryl group, provided that when n is 2 or more, each A' is the same or different; B' is a hydroxyl, halogen, $C_{1-3}$ alkoxy or $C_{6-15}$ aryloxy group, provided that when n is 2 or less, each B' is the same or different; and n is an integer between 0 and 3, in an organic solvent in the presence of an acid or base catalyst.

Preferred compounds of Formula 8 which can be used in the present invention are TS-T4 (OH), TS-T4 (OMe), TS-T4Q4, TS-T4T4 and TS-Q4 below:

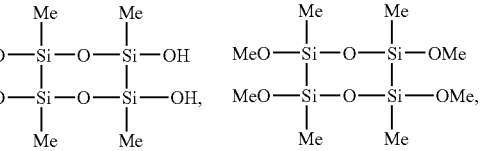

TS-T4(OH)           TS-T4(OMe)

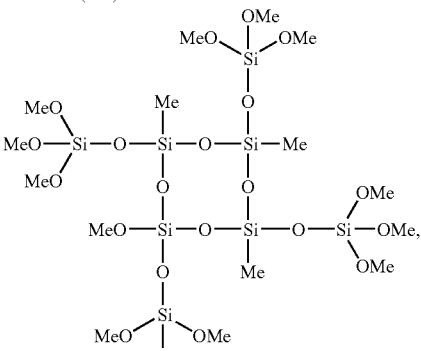

TS-T4Q4

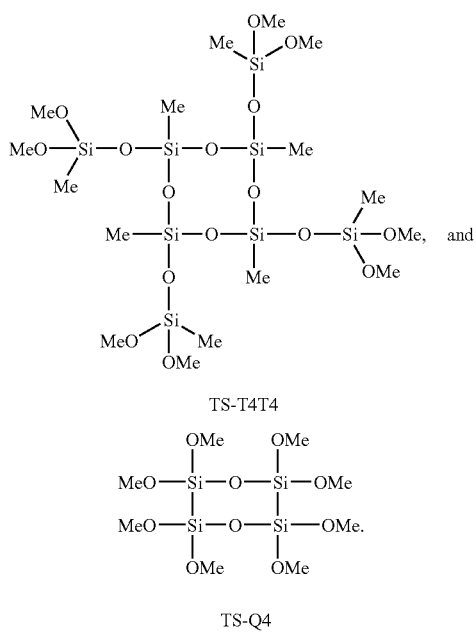

TS-T4T4

TS-Q4

A preferred example of the compound of Formula 9 is TCS-2 below:

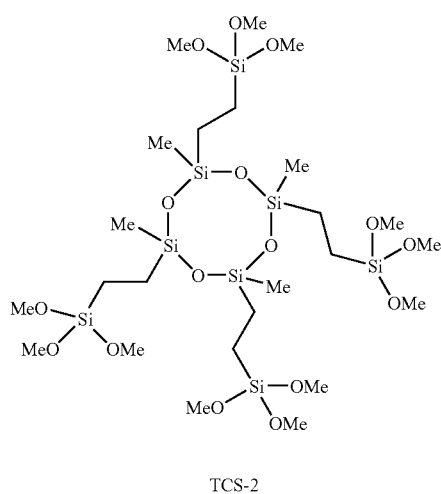

TCS-2

A preferred example of the compound of Formula 10 is BTMSE:

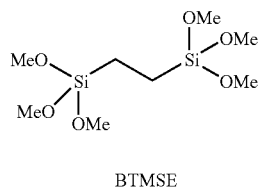

BTMSE

Preferred compounds of Formula 11 which can be used in the present invention are MTMS and TMOS below:

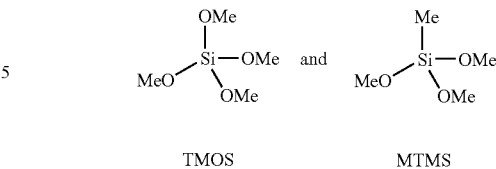

TMOS     MTMS

The polymer prepared from the multi-functional linear siloxane compound of Formula 1 can be easily formed into a ladder structure depending on its structure when polymerized. Accordingly, the polymer can exhibit excellent physical properties, such as modulus and toughness, and can maintain its hygroscopicity at a low level. In addition, when the compound of Formula 7 having a "Q"-shaped structure incorporated in the backbone chain is polymerized with a siloxane monomer having a ladder structure, e.g., TS-T4 (OMe), a ladder structure can be easily introduced into the polymers to be prepared. The polymers thus prepared have better physical properties than polymers prepared by conventional processes. In addition, since the polymers are highly compatible with conventional pore-forming materials, they can be very useful in forming dielectric films having low dielectric constants.

When the siloxane compound of Formula 1 is polymerized with at least one comonomer selected from the compounds of Formulae 8 to 11, the molar ratio between the monomers is properly determined according to intended characteristics of the dielectric film to be formed, but there are no particular limitations on the molar ratio. For example, when the linear siloxane compound of Formula 1 and another comonomer are polymerized to prepare a copolymer, the molar ratio of the siloxane compound to the comonomer is between 1:99 and 99:1.

Examples of suitable organic solvents used to prepare the siloxane polymer of the present invention include, but are not limited to, aliphatic hydrocarbon solvents, such as hexane, heptane, etc.; aromatic hydrocarbon solvents, such as anisol, mesitylene, xylene, etc.; ketone-based solvents, such as methyl isobutyl ketone, cyclohexanone, acetone, etc.; ether-based solvents, such as tetrahydrofuran, isopropyl ether, etc.; acetate-based solvents, such as ethyl acetate, butyl acetate, propylene glycol methyl ether acetate, etc.; alcohol-based solvents, such as isopropyl alcohol, butyl alcohol, etc.; amide-based solvents, such as 1-methyl-2-pyrrolidinone, dimethylacetamide, dimethylformamide, etc.; silicon-based solvents; and mixtures thereof.

Examples of acid catalysts usable in the present invention include, but are not particularly limited to, any acid catalysts which can be used to prepare polysilsesquioxanes, and are preferably hydrochloric acid, nitric acid, benzene sulfonic acid, oxalic acid and formic acid. Examples of base catalysts usable in the present invention include, but are not particularly limited to, any base catalysts that may be used to prepare polysilsesquioxanes, and are preferably potassium hydroxide, sodium hydroxide, triethylamine, sodium bicarbonate and pyridine. The molar ratio of the total monomers to the catalyst used is in the range of $1:1\times10^{-6}$ to 1:10. The molar ratio of the total monomers to water is in the range of 1:1 to 1:1000. The hydrolysis and the polycondensation can be carried out under appropriate time and temperature conditions, and are preferably carried out at 0~200° C. for 0.1~100 hours.

The weight average molecular weight of the siloxane polymer is preferably in the range of 3,000~300,000, but is not particularly limited to this range.

Formation of the Dielectric Film

Additionally, the present invention provides a process for forming a dielectric film comprising the steps of i) dissolving the siloxane polymer or copolymer, and if necessary, a pore-forming material to prepare a coating solution; and ii) applying the coating solution onto a substrate, followed by heat-curing.

Examples of pore-forming materials usable in the present invention include any pore-forming materials that may be used to form porous dielectric films, and are preferably cyclo-dextrins, polycaprolactones, Brij surfactants, polyethylene glycol-polypropylene glycol-polyethylene glycol triblock copolymer surfactants and derivatives thereof. These compounds may be used alone or as a mixture of two or more thereof. The pore-forming material is preferably present in an amount of 0~70% by weight, based on the total weight of the solid matters (namely, the siloxane polymer and the pore-forming material) of the coating solution, but is not limited to this range.

Organic solvents usable to prepare the coating solution include, but are not particularly limited to, all organic solvents described above. The solid content of the coating solution is in the range of 0.1~80% by weight, preferably 5~70% by weight and more preferably 5~30% by weight, based on the total weight of the coating solution, but is not particularly limited to the above ranges. When the solid content is less than 0.1% by weight, a film as thin as 1,000 Å or less is undesirably formed. On the other hand, when the solid content exceeds 80% by weight, the solid matters, particularly the siloxane polymer, may be incompletely dissolved.

It is to be understood that various substrates can be used without limitation so far as they do not detract from the object of the present invention. Examples of substrates usable in the present invention include any substrates which are capable of withstanding the heat-curing conditions employed. Glass, silicon wafer and plastic substrates can be used according to the intended application. In the present invention, the application of the coating solution may be carried out by spin coating, dip coating, spray coating, flow coating and screen printing techniques, but is not especially limited thereto. In view of ease of application and thickness uniformity, the most preferred coating technique is spin coating. Upon spin coating, the coating speed is preferably adjusted within 800~5,000rpm.

Optionally, the organic solvent used is evaporated to dry the film after application of the coating solution. The film drying can be conducted by exposing the film to atmosphere, subjecting the film to a vacuum in the initial stage of the subsequent heat-curing step, or mildly heating the film to a temperature of 200° C. or lower.

In step ii), the film is heat-cured at a temperature of 150~600° C. and preferably 200~450° C. for 1~180 minutes, thereby forming a crack-free insoluble coating film. The term "crack-free thin film" as used herein is defined as a coating film including no cracks when observed by an optical microscope with a magnification of 1,000×. As used herein, the term "insoluble coating film" refers to a coating film substantially insoluble in solvents used to deposit the siloxane polymer or solvents known to be useful in applying a resin onto a substrate. When the coating solution contains a pore-forming material, the heat-curing temperature is properly determined considering the decomposition temperature of the pore-forming material.

Since the dielectric film formed by using the siloxane polymer alone has a dielectric constant of 3.0 or less, it can be suitable for use as a semiconductor interlayer low dielectric coating film. The dielectric film formed by using a mixture of the siloxane polymer and the pore-forming material has a dielectric constant of 2.5 or less. Since the dielectric film formed by the method of the present invention has excellent mechanical properties, such as toughness and elasticity, and a low carbon content, it can be useful as a semiconductor interlayer dielectric film.

Hereinafter, the present invention will be described in more detail with reference to the following examples. However, these examples are given for the purpose of illustration and are not to be construed as limiting the scope of the invention.

EXAMPLES

First, procedures for measuring the performance of dielectric films formed in the following examples are described.

1. Measurement of Dielectric Constant:

First, a thermally oxidized silicon film is applied onto a boron-doped p-type silicon wafer to a thickness of 3,000 Å, and then a 100 Å-thick titanium film, a 2,000 Å-thick aluminum film and a 100 Å-thick titanium film are sequentially deposited on the silicon film using a metal evaporator. Thereafter, a dielectric film is coated onto the resulting structure, after which a 100 Å-thick spherical titanium thin film (diameter: 1 mm) and a 5,000 Å-thick aluminum thin film (diameter: 1 mm) are sequentially deposited on the dielectric film using a hardmask designed to have an electrode diameter of 1 mm, to form a MIM (metal-insulator-metal)-structured low dielectric constant thin film for dielectric constant measurement. The capacitance of the thin film is measured at around 10 kHz, 100 kHz and 1 MHz using a PRECISION LCR METER (HP4284A) accompanied with a probe station (Micromanipulatior 6200 probe station). The thickness of the thin film is measured using a prism coupler. The dielectric constant (k) of the thin film is calculated according to the following equation:

$$k = C \times d / \in_o \times A$$

in which k is the relative permittivity, C is the capacitance of the dielectric film, $\in_o$ is the permittivity of a vacuum (8.8542×10$^{-12}$ Fm$^{-1}$), d is the thickness of the dielectric film, and A is the contact cross-sectional area of the electrode.

2. Hardness and Modulus:

The hardness and modulus of a dielectric thin film is determined by quantitative analysis using a Nanoindenter II (MTS). Specifically, after the thin film is indented into the Nanoindenter until the indentation depth reaches 10% of its overall thickness, the hardness and modulus of the dielectric thin film are measured. At this time, the thickness of the thin film is measured using a prism coupler. In order to secure better reliability of these measurements in the following Examples and Comparative Examples, the hardness and modulus are measured at a total of 9 indention points on the dielectric film, and the obtained values were averaged.

3. Carbon Content:

In the following Examples and Comparative Examples, the carbon content of dielectric films is measured by XPS (X-ray photoelectron spectroscopy) using a Q2000 (Physical Electronics). As an X-ray generating apparatus, a monochromatic Al source (1486.6 eV) is used. Specifically, after the thin films are sputtered using Ar ions at 3 keV, element quantitative analysis is performed at each depth. Values measured at a certain depth where the content of each element was maintained to be constant were averaged, and the obtained average value was determined as a carbon content.

Synthesis of Monomers

1) Synthesis of Multi-Functional Linear Siloxane Monomer (L5):

0.444 moles (17.767 g) of sodium hydroxide and 200 ml of tetrahydrofuran (THF) are placed in a reaction flask. After the mixture is cooled to 0° C., 1.3 moles (200 ml) of vinyltrimethoxysilane is added thereto. The temperature of the reaction mixture is gradually raised to room temperature. At this temperature, the reaction is allowed to proceed for 12 hours. Volatile materials are completely evaporated at a pressure of ca. 0.1 torr to obtain sodium silanolate as a solid. The solid salt is dissolved in 800 ml of THF. After the resulting solution is cooled to 0° C., 40 g of dichlorodiethoxysilane (purity: 90%, Gelest Co.) is slowly added thereto. After completion of the addition, the mixture is reacted at room temperature for 12 hours. The reaction mixture is evaporated at a pressure of ca. 0.1 torr to remove volatile materials, dissolved in 800 ml of hexane, and filtered through celite. Hexane is removed by distillation at reduced pressure to afford a liquid compound represented by the following formula:

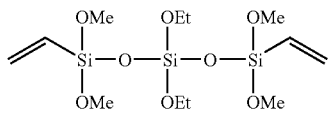

[1H NMR (300 MHz) data (CDCl₃): δ 1.17~1.21 (t, 6H, —O—C—CH₃), 3.53 (s, 12H, 4×OCH₃), 3.78~3.82 (q, 4H, 2×—OCH₂—), 5.85~6.08 (m, 6H, 2×—CH=CH₂)].

0.11 moles (41.85 g) of the liquid compound and a solution of 0.46 g of platinum(0)-1,3-divinyl-1,1,3,3-tetramethyldisiloxane complex in xylene are charged into a flask, and then the resulting mixture is diluted in 300 ml of THF. To the dilution is slowly added 0.33 moles (40.3 g) of trimethoxysilane. The reaction is continued at 50° C. for 48 hours. After the reaction solution is cooled to room temperature, volatile materials are completely evaporated at a pressure of ca. 0.1 torr. 300 ml of hexane and log of activated carbon are added to the concentrate. After the resulting mixture is stirred for 6 hours, it is filtered through celite. Hexane is removed by distillation at a pressure of 0.1 torr to afford 60.4 g (yield: 87.9%) of the multi-functional linear siloxane compound L5 represented by the following formula:

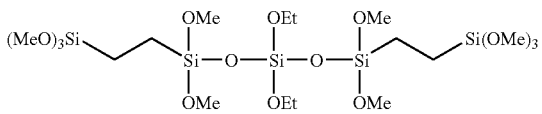

[1H NMR (CDCl₃) (300 MHz) data: δ 0.52~0.64 (m, 5.7H of 8H, —CH₂CH₂— and —Si—CH—Si—, kinetic product), 1.13~1.22 (t, 6H, —O—C—CH₃), 1.13~1.22 (d, 2.3 H of 8H, —Si—CCH₃—Si—, thermodynamic product), 3.53 (s, 30H, 10×OCH₃), 3.80~3.87 (q, 4H, 2×—OCH₂—)]

2) Synthesis of Multi-Functional Linear Siloxane Monomer (L6):

A solution of 7.27 mmol (1.29 g) of palladium (II) dichloride [PdCl₂ (II)] in 30 ml of carbon tetrachloride is placed in a flask, and then 0.106 moles (24 g) of 1,1,1,3,3-pentamethoxy-1,3-disilapropane (98%, Korea Institute of Science and Technology (KIST)) is slowly added thereto at 0° C. The reaction is allowed to proceed at this temperature for 4 hours. The reaction mixture is filtered through celite to obtain 3-chloro-1,1,1,3,3-pentamethoxy-1,3-disilapropane.

Thereafter, 0.12 moles (2.88 g) of sodium hydroxide and 200 ml of tetrahydrofuran are charged into the flask. After the temperature of the flask is lowered to 0° C., 0.31 moles (45 ml) of methyltrimethoxysilane is added thereto. The mixture is slowly warmed to room temperature. The reaction is further continued for 12 hours. Thereafter, volatile materials are completely evaporated at a pressure of ca. 0.1 torr to obtain sodium silanolate as a solid. The solid salt is dissolved in 200 ml of THF. After the resulting solution is cooled to 0° C., the 3-chloro-1,1,1,3,3-pentamethoxy-1,3-disilapropan previously prepared above is slowly added thereto. After completion of the addition, the reaction is continued at room temperature for 12 hours. The reaction mixture is evaporated at a pressure of ca. 0.1 torr to remove volatile materials, dissolved in 200 ml of hexane, and filtered through celite. Hexane is removed by distillation at reduced pressure to afford 28.5 g (yield: 77.5%) of liquid compound L6 represented by the following formula:

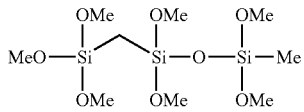

[1H NMR (CDCl₃) (300 MHz) data: δ 0.14~0.03 (m, 5H, 1×CH₂ and 1×CH₃), 3.50 (s, 21H, 7×OCH3)]

3) Synthesis of Comonomer TS-T4 (OMe):

A solution of 40 mmol (7.09 g) of palladium (II) dichloride [PdCl₂ (II)] is dissolved in 70 ml of carbon tetrachloride, and then 0.1442 moles (35 ml) of 2,4,6,8-tetramethyl-2,4,6,8-cyclotetrasiloxane is slowly added thereto at 0° C. The reaction is allowed to proceed at this temperature for 4 hours. The reaction mixture is filtered through activated carbon and celite. The obtained filtrate is diluted in 700 ml of THF, and then 0.631 moles (88 ml) of triethylamine is added thereto. After the resulting mixture is cooled to 0° C., 0.69 moles (28 ml) of methanol is slowly added thereto. The temperature is raised to room temperature, and the reaction is continued for 15 hours. The reaction mixture is filtered through activated carbon and celite. Volatile materials are removed by distillation at reduced pressure (ca. 0.1 torr) to afford liquid monomer TS-T4 (OMe) represented by the following formula:

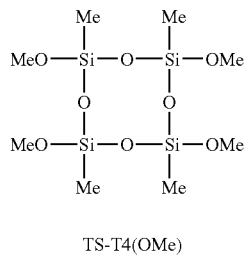

TS-T4(OMe)

The analytical results of the ¹H-NMR spectrum (300 MHz) of the monomer are as follows: δ 0.067 (s, 12H, 4×[—CH₃]), 3.55 (s, 3H, 4×[—OCH₃]).

4) Synthesis of Comonomer TCS-2:

29.01 mmol (10.0 g) of 2,4,6,8-tetramethyl-2,4,6,8-tetravinylcyclotetrasiloxane and a solution of 0.164 g of platinum (0)-1,3-divinyl-1,1,3,3-tetramethyldisiloxane complex in xylene are charged into a flask, and then the resulting mixture is diluted in 300 ml of diethyl ether. After the reaction solution is cooled to −78° C., 127.66 mmol (17.29 g) of trichlorosilane is slowly added thereto. After the temperature of the flask is gradually raised to room temperature, the reaction is allowed to proceed for 40 hours. The reaction solution is concentrated at reduced pressure (ca. 0.1 torr) to remove volatile materials. 100 ml of hexane is added to the concentrate. After the resulting mixture is stirred for 1 hour, it is filtered through celite. Hexane is removed by distillation at a pressure of ca. 0.1 torr to obtain a liquid reaction product.

11.56 mmol (10.0 g) of the liquid reaction product is diluted in 50 ml of THF, and then 138.71 mmol (13.83 g) of triethylamine is added thereto. The reaction temperature is lowered to −78° C. After 136.71 mmol (4.38 g) of methanol is slowly added to the solution, the reaction temperature is slowly raised to room temperature. The reaction is allowed to proceed for 15 hours. The reaction mixture is filtered through celite. The obtained filtrate is concentrated at reduced pressure (ca. 0.1 torr) to remove volatile materials. After 100 ml of hexane is added to the concentrate, the resulting mixture is stirred for 1 hour, filtered through celite, and then 5 g of activated carbon is added thereto. After the mixture is stirred for 10 hours, it is filtered through celite. Hexane is removed by distillation at reduced pressure (ca. 0.1 torr) to afford colorless liquid monomer TCS-2 represented by the following formula:

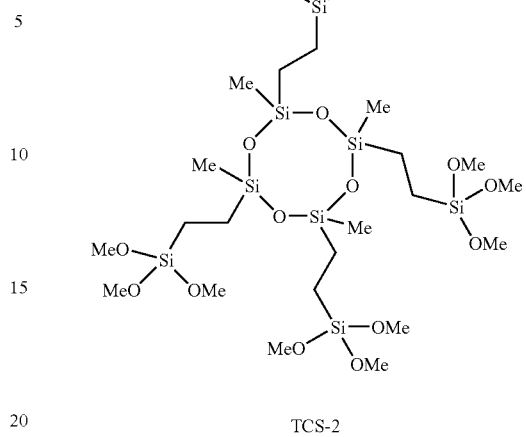

TCS-2

The analytical results of the ¹H-NMR spectrum (300 MHz, acetone-d₆) of the monomer are as follows: δ 0.09 (s, 12H, 4×[—CH₃]), 0.52~0.64 (m, 16H, 4×[—CH₂CH₂—]), 3.58 (s, 36H, 4×[—OCH₃]₃).

Preparation of Copolymers

As shown in Table 1 below, the multi-functional linear siloxane monomers L5 and L6 prepared in Preparative Examples 1) and 2), and TS-T4 (OMe) and TCS-2 prepared in Preparative Examples 3) and 4), respectively, and commercially available MTMS (methyltrimethoxy silane, Sigma Aldrich) as comonomers are used to prepare polymers (a) to (i). For the purpose of comparison, TCS-2 and MTMS are used to prepare polymer (j).

The respective copolymers were prepared in accordance with the following procedure. First, selected monomers are charged into a flask, and are then diluted in THF in the amount of 12 times the amount of monomers used. After the temperature of the dilution is lowered to −78° C., HCl and water are added to the dilution. At an elevated temperature of 70° C., the reaction is allowed to proceed for 12 hours. The reaction solution is transferred to a separatory funnel, followed by addition of diethylether in the same amount as that of THF. The resulting mixture is washed three times with water in the amount of about one tenth of the total volume of the solvents used, and is then distilled at reduced pressure to remove volatile materials, yielding a corresponding polymer as a white powder. The polymer is dissolved in tetrahydrofuran until it is transparent, and filtered through a filter (pore size: 0.2 μm). Water is added to the filtrate to obtain a white precipitate. The precipitate is dried at 0~20° C. and 0.1 torr for 10 hours to afford a corresponding siloxane polymer.

TABLE 1

| Polymer | Monomers (mmol) | | | | | HCl (mmol) | H₂O (mmol) | Amount of Polymer (g) |
| | L5 | L6 | TS-T4 (OMe) | TCS-2 | MTMS | | | |
| --- | --- | --- | --- | --- | --- | --- | --- | --- |
| (a) | 6.61 | | 6.61 | | | 1.059 | 353 | 3.52 |
| (b) | 4.77 | | 9.54 | | | 0.954 | 318 | 3.27 |
| (c) | 6.56 | | 9.84 | | | 1.181 | 393 | 3.06 |
| (d) | 7.80 | | 2.60 | | | 1.040 | 346 | 2.55 |

TABLE 1-continued

| Polymer | Monomers (mmol) | | | | | HCl (mmol) | H₂O (mmol) | Amount of Polymer (g) |
| | L5 | L6 | TS-T4 (OMe) | TCS-2 | MTMS | | | |
|---|---|---|---|---|---|---|---|---|
| (e) | 8.02 | | | | 8.02 | 1.203 | 180 | 2.90 |
| (f) | 7.95 | | | | 18.5 | 1.510 | 227 | 3.82 |
| (g) | 5.57 | | | | 50.1 | 2.170 | 724 | 3.27 |
| (h) | | 20.2 | | | 20.2 | 2.060 | 688 | 6.02 |
| (i) | | 5.61 | | 5.61 | | 1.062 | 354 | 2.10 |
| (j) | | | | 4.80 | 43.2 | 1.872 | 629 | 5.93 |

Formation of Dielectric Films

As shown in Table 2 below, the respective dielectric films are formed in accordance with the following procedure. First, the siloxane polymer and heptakis(2,3,6-tri-methoxy)-β-cyclodextrin as a pore-forming material are used to prepare a thin film composition. The composition is dissolved in propyleneglycol methyletheylether acetate to prepare a coating solution. When the siloxane polymer alone is used to form a dielectric film, the solid content is fixed to 25% by weight. On the other hand, when the polymer and the pore-forming material are used, the solid content is fixed to 27% by weight. The coating solution is spin-coated on a silicon wafer at 3,000 rpm for 30 seconds, and pre-baked on a hot plate under nitrogen atmosphere at 150° C. for 1 minute and at 250° C. for 1 minute, sequentially. The pre-baked silicon wafer is dried to form a film. The film is baked under a nitrogen atmosphere while heating to 420° C. for 1 hour at a rate of 3° C./min.).

The thickness, refractive index, dielectric constant, hardness, modulus and carbon content of the dielectric films thus formed are measured. The results are shown in Table 2 below.

and MTMS. Accordingly, the dielectric films are advantageously applicable to semiconductor processes.

As apparent from the above description, the siloxane compound of the present invention is highly reactive. In addition, the siloxane polymer prepared from the siloxane compound not only has satisfactory mechanical properties, thermal stability and crack resistance, but also exhibits a low hygroscopicity and excellent compatibility with pore-forming materials, which leads to a low dielectric constant. Furthermore, the siloxane polymer retains a relatively low carbon content but a high SiO₂ content, resulting in its improved applicability to semiconductor processes. Therefore, the siloxane polymer can be advantageously used as a material for dielectric films of semiconductor devices.

Although the preferred embodiments of the present invention have been disclosed for illustrative purposes, those skilled in the art will appreciate that various modifications,

TABLE 2

| Dielectric film Nos. | Composition of coating solution | | Thickness (Å) | Refractive index | Dielectric constant | Hardness (GPa) | Modulus (GPa) | Carbon content (%) |
| | Siloxane polymer (wt %) | Pore-forming material (wt %) | | | | | | |
|---|---|---|---|---|---|---|---|---|
| A | (a) 100 | — | 8595 | 1.410 | 3.11 | 1.87 | 10.54 | 19.62 |
| A-1 | (a) 70 | 30 | 7990 | 1.297 | 2.17 | 0.65 | 4.00 | 17.05 |
| B | (b) 100 | — | 9976 | 1.406 | 3.04 | 1.50 | 8.69 | 18.38 |
| B-1 | (b) 70 | 30 | 9133 | 1.296 | 2.21 | 0.50 | 3.07 | 16.41 |
| C | (c) 100 | — | 8627 | 1.4217 | 2.68 | 1.76 | 9.69 | 16.52 |
| C-1 | (c) 70 | 30 | 8682 | 1.306 | 2.28 | 0.65 | 3.99 | 12.08 |
| F | (f) 100 | — | 9129 | 1.420 | 3.42 | 2.21 | 12.78 | 21.05 |
| F-1 | (f) 70 | 30 | 9389 | 1.301 | 2.30 | 0.80 | 5.16 | 16.61 |
| G | (g) 100 | — | 6184 | 1.405 | 2.82 | 1.67 | 9.47 | 19.21 |
| G-1 | (g) 70 | 30 | 6431 | 1.302 | 2.15 | 0.73 | 4.23 | 17.83 |
| H | (h) 100 | — | 10888 | 1.410 | 3.74 | 2.17 | 13.06 | 16.36 |
| H-1 | (h) 70 | 30 | 11221 | 1.276 | 2.12 | 0.66 | 4.22 | 11.78 |
| I | (i) 100 | — | 14213 | 1.425 | — | 1.52 | 8.29 | 24.30 |
| I-1 | (i) 70 | 30 | 10258 | 1.318 | 2.23 | 0.59 | 3.43 | 21.67 |
| J | (j) 100 | — | 11654 | 1.415 | 2.70 | 1.13 | 5.90 | 29.0 |
| J-1 | (j) 70 | 30 | 9811 | 1.335 | 2.24 | 0.50 | 2.86 | 25.6 |

As can be seen from Table 2, the dielectric films formed by using the copolymers prepared from the multi-functional linear siloxane monomer L5 or L6 exhibited a similar dielectric constant, but a high hardness, a high modulus and a low carbon content, compared to the dielectric film formed by using the copolymer prepared from previously known TCS-2 additions and substitutions are possible, without departing from the spirit and scope of the invention as disclosed in the accompanying claims.

What is claimed is:

1. A multi-functional linear siloxane compound represented by any one of Formulae 5 to 7 below:

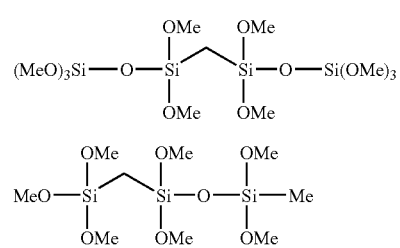
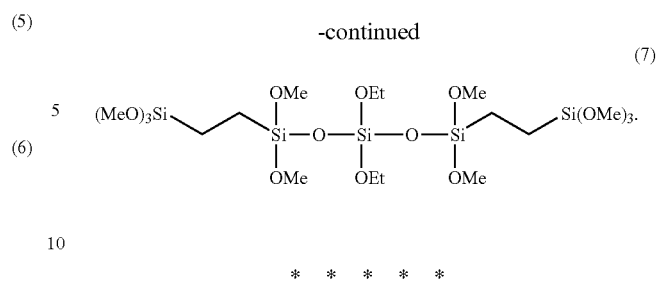
* * * * *